United States Patent
Lv et al.

(10) Patent No.: US 11,596,407 B2
(45) Date of Patent: Mar. 7, 2023

(54) MAGNETIC VASCULAR ANASTOMOSIS DEVICE FOR RAPID LIVER TRANSPLANTATION

(71) Applicant: The First Affiliated Hospital, Medical School of Xi'an Jiaotong University, Xi'an (CN)

(72) Inventors: Yi Lv, Xi'an (CN); Xiaopeng Yan, Xi'an (CN); Shanpei Wang, Xi'an (CN); Aihua Shi, Xi'an (CN); Xuemin Liu, Xi'an (CN); Zheng Wu, Xi'an (CN); Bo Wang, Xi'an (CN); Rongqian Wu, Xi'an (CN); Xiaogang Zhang, Xi'an (CN); Feng Ma, Xi'an (CN); Kang Liu, Xi'an (CN); Qiang Lu, Xi'an (CN)

(73) Assignee: The First Affiliated Hospital, Medical School of Xi'an Jiaotong University, Xi'an (CN)

( * ) Notice: Subject to any disclaimer, the term of this patent is extended or adjusted under 35 U.S.C. 154(b) by 543 days.

(21) Appl. No.: 16/775,261

(22) Filed: Jan. 28, 2020

(65) Prior Publication Data

US 2020/0375600 A1 Dec. 3, 2020

(30) Foreign Application Priority Data

May 29, 2019 (CN) .......................... 201910457909.2
May 29, 2019 (CN) .......................... 201920791946.2

(51) Int. Cl.
*A61B 17/11* (2006.01)
*A61B 17/00* (2006.01)

(52) U.S. Cl.
CPC ...... *A61B 17/11* (2013.01); *A61B 2017/00778* (2013.01); *A61B 2017/00876* (2013.01);
(Continued)

(58) Field of Classification Search
CPC ................ A61B 17/11; A61B 17/1114; A61B 2017/00778; A61B 2017/00876;
(Continued)

(56) References Cited

U.S. PATENT DOCUMENTS 6,352,543 B1 * 3/2002 Cole ...................... A61B 17/11
  606/153
6,652,540 B1 * 11/2003 Cole ........................ A61F 2/94
  606/151

(Continued)

*Primary Examiner* — Ryan J. Severson
(74) *Attorney, Agent, or Firm* — Novoclaims Patent Services LLC; Mei Lin Wong

(57) ABSTRACT

A magnetic vascular anastomosis device for rapid liver transplantation includes a magnetic ring assembly and a base member assembly. The magnetic ring assembly includes an O-shaped magnetic ring and a C-shaped magnetic ring coupled at a donor liver blood vessel and a receptor liver blood vessel respectively. The base member assembly includes an O-shaped base member and a C-shaped base member. The base member is categorized into a slotted base member, a columned base member, and a hooked base member for different surgical suture methods. The magnetic vascular anastomosis device incorporates with the magnetic attraction between magnetic rings, such that the entire liver transplantation vascular anastomosis process is fast, safe, and reliable. The vascular anastomosis device is able apply for different operations involving vascular anastomosis such as kidney transplantation, lung transplantation, heart transplantation, and maxillofacial surgery.

20 Claims, 5 Drawing Sheets

(52) U.S. Cl.
CPC ............... *A61B 2017/00969* (2013.01); *A61B 2017/1107* (2013.01); *A61B 2017/1132* (2013.01)

(58) Field of Classification Search
CPC .. A61B 2017/00969; A61B 2017/1103; A61B 2017/1107; A61B 2017/1132
See application file for complete search history.

(56) References Cited

U.S. PATENT DOCUMENTS

| | | | | |
|---|---|---|---|---|
| 6,719,768 B1* | 4/2004 | Cole | ................... | A61B 17/0057 606/153 |
| 6,802,847 B1* | 10/2004 | Carson | ............... | A61B 17/0643 606/153 |
| 6,932,827 B2* | 8/2005 | Cole | ..................... | A61F 2/2493 606/153 |
| 7,232,449 B2* | 6/2007 | Sharkawy | ................. | A61F 2/90 606/153 |
| 7,431,727 B2* | 10/2008 | Cole | ................... | A61B 17/0057 606/153 |
| 7,938,841 B2* | 5/2011 | Sharkawy | ............. | A61B 17/11 606/153 |
| 8,142,454 B2* | 3/2012 | Harrison | ............. | A61B 17/0483 606/153 |
| 8,518,062 B2* | 8/2013 | Cole | ................... | A61B 17/0057 606/153 |
| 8,623,036 B2* | 1/2014 | Harrison | ............. | A61B 17/1114 606/153 |
| 2002/0103495 A1* | 8/2002 | Cole | ....................... | A61B 17/11 606/153 |
| 2002/0143347 A1* | 10/2002 | Cole | ....................... | A61B 17/11 606/153 |
| 2004/0034377 A1* | 2/2004 | Sharkawy | ............... | A61F 2/064 606/153 |
| 2005/0021059 A1* | 1/2005 | Cole | ......................... | A61F 2/94 606/153 |
| 2005/0080439 A1* | 4/2005 | Carson | ................... | H01F 41/026 606/153 |
| 2005/0192603 A1* | 9/2005 | Cole | ..................... | H01F 41/026 606/153 |
| 2006/0282106 A1* | 12/2006 | Cole | ................... | A61B 17/0643 606/153 |
| 2007/0010834 A1* | 1/2007 | Sharkawy | ............... | A61B 17/11 606/153 |
| 2008/0114384 A1* | 5/2008 | Chang | ................... | A61B 17/1114 606/153 |
| 2009/0048618 A1* | 2/2009 | Harrison | ............. | A61B 17/8076 600/12 |
| 2011/0184505 A1* | 7/2011 | Sharkawy | ............. | H01F 41/026 623/1.11 |

* cited by examiner

MAGNETIC VASCULAR ANASTOMOSIS DEVICE FOR RAPID LIVER TRANSPLANTATION

CROSS REFERENCES OF RELATED APPLICATIONS

This is a non-provisional application which claims foreign priority of application number 201910457909.2 with a filing date of May 29, 2019 in China (CN); and application number 201920791946.2 with a filing date of May 29, 2019 in China (CN). The content of these specification, including any intervening amendments thereto, are incorporated herein by reference.

BACKGROUND OF THE PRESENT INVENTION

Field of Invention

The present invention relates a field of clinical medical equipment, and more particularly to a magnetically assisted vascular anastomosis device.

Description of Related Arts

In view of blood vessel surgery, such as during the liver transplantation or bypass surgery of portal hypertension, a trained surgeon needs 10 to 15 minutes as an anastomotic time to complete each vena cave anastomosis, and needs 30 to 60 minutes for the anhepatic phase. However, the anastomotic time is too long, and the portal vein and hepatic artery cannot be opened at the same time, such that the hemodynamic system and the homeostasis may be disordered. Accordingly, it still needs 10 minutes for anastomosis of the hepatic artery again after the portal vein is opened, such that it may cause the hot ischemic again for hepatobiliary tract. This is an important reason for the high biliary complications after liver transplantation. The shorter the anhepatic period in liver transplantation, the more stable the hemodynamics, and the faster the recovery of liver function. In order to enhance the quality and speed of anastomosis, and to reduce the anastomosis difficulty and postoperative complications, the anastomosis technology and the quality of sutures are continuously improved. However, the conventional manual suture techniques has the drawbacks of the manual suturing skill for the healing of the anastomosis. According to the existing development of the liver transplantation technology, it is impossible to solve the above problems by simply improving the manual suture technology. The research on anastomosis ring and magnetic anastomosis device has made significantly to achieve a good result for anastomosis of small and medium vessels in clinically use. However, for the large diameter of the liver superior and inferior vena cava, the anastomosis operation space is small and limited, and the operation thereof is difficult, such that there is no current anastomosis device for operating effectively. Accordingly, there is an urgent need to provide a vascular anastomosis device in order to overcome the above technical problems.

SUMMARY OF THE PRESENT INVENTION

In order to solve the above technical problems, an objective of the present invention is to provide a magnetic vascular anastomosis device for rapid liver transplantation by using the magnetic attraction between magnetic rings, such that through the present invention, the entire liver transplantation vessel anastomosis process is fast, safe, and reliable.

In order to achieve the above objective, the present invention provides a magnetic vascular anastomosis device for rapid liver transplantation, comprising:

a O-shaped magnetic ring 1, which has a cylindrical shape or an oval shape;

a C-shaped magnetic ring 2 having a longitudinal through notch 20 extended from an inner circumferential wall of the C-shaped magnetic ring 2 to an outer circumferential wall thereof, wherein a cross sectional shape of the O-shaped magnetic ring 1 is the same as a cross sectional shape of the C-shaped magnetic ring 2;

a O-shaped base member comprising a O-shaped base body 100 having a central through slot 101, a O-shaped protrusion 5 extended from the base body at a position around the central through slot 101, and a structure for proline threading provided at the O-shaped base body 100 outside the O-shaped protrusion 5, wherein a cross sectional shape of the O-shaped protrusion 5 is the same as the cross sectional shape of the O-shaped magnetic ring 1, wherein a cross sectional size of the O-shaped protrusion 5 is equal or slightly smaller than a cross sectional size of the O-shaped magnetic ring 1; and a C-shaped base member comprising a C-shaped base body 200 having a central through slot 201, a C-shaped protrusion 15 extended from the base body at a position around the central through slot 201, and a structure for proline threading provided at the C-shaped base body 200 outside the C-shaped protrusion 15, wherein a cross sectional shape of the C-shaped protrusion 15 is the same as a cross sectional shape of the C-shaped magnetic ring 2, wherein a cross sectional size of the C-shaped protrusion 15 is equal or slightly smaller than a cross sectional size of the C-shaped magnetic ring 2, wherein the C-shaped protrusion 15 and the C-shaped base body 200 form a through gap 202, wherein the C-shaped base member further comprises a positioning member 16 integrally, outwardly and radially extended from the C-shaped protrusion 15, wherein a width of the positioning member 16 is equal or slightly smaller than a width of the longitudinal through notch 20 of the C-shaped magnetic ring 2.

Each of the O-shaped magnetic ring 1 and the C-shaped magnetic ring 2 is made of neodymium iron boron, aluminum nickel cobalt, ferrite or samarium cobalt, etc. The surface of each of the O-shaped magnetic ring 1 and the C-shaped magnetic ring 2 is treated and coated with titanium nitride, polytetrafluoroethylene or parylene. An outer diameter of each of the O-shaped magnetic ring 1 and the C-shaped magnetic ring 2 matches with an inner diameter of the blood vessel to be anastomosed. Each of the C-shaped base member and the C-shaped base member is made of metal material or a polymer material, and the surface of each of the C-shaped base member and the C-shaped base member is treated and coated with titanium nitride, polytetrafluoroethylene, or parylene.

For the O-shaped base member, the structure for proline threading comprises a plurality of first axial holes 4 outwardly and evenly distributed at an outer circumferential portion of the O-shaped base body 100 to form a O-shaped slotted base member 3. Alternatively, the structure for proline threading comprises a plurality of radial columns 7 outwardly and evenly distributed at an outer circumferential portion of the base member to form a O-shaped columned base member 6. Alternatively, the structure for proline threading comprises a plurality of first hooks 9 downwardly, axially and evenly distributed at a bottom side of the O-shaped base body 100 to form a O-shaped hooked base member 8.

For the C-shaped base member, the structure for proline threading comprises a plurality of radial holes 17 outwardly and evenly distributed at an outer circumferential portion of the C-shaped base body 200 to form a C-shaped slotted base member 10. Alternatively, the structure for proline threading comprises a plurality of radial columns 18 outwardly and evenly distributed at an outer circumferential portion of the C-shaped base body 200 to form a C-shaped columned base member 11. Alternatively, the structure for proline threading comprises a plurality of second hooks 19 downwardly, axially and evenly distributed at a bottom side of the C-shaped base body 200 to form a C-shaped hooked base member 12, wherein hooking ends of the second hooks 19 are extended toward a center of the central through slot 201 of the C-shaped base body 200.

The O-shaped magnetic ring 1 is sleeved or coaxially coupled with the O-shaped protrusion 5 to form a O-shaped magnetic assembling ring 13. The C-shaped magnetic ring 2 is sleeved or coaxially coupled with the C-shaped protrusion 15 to form a C-shaped magnetic assembling ring 14. A magnetic pole of an exposed side of the O-shaped magnetic ring 1 is opposite to a magnetic pole of an exposed side of the C-shaped magnetic ring 2, such that the O-shaped magnetic ring 1 and the C-shaped magnetic ring 2 are magnetic attracted with each other.

According to the present invention, comparing with the conventional device, the magnetic vascular anastomosis device incorporates with the magnetic attraction between magnetic rings to achieve rapid preliminary anastomosis of large diameter blood vessel in liver transplantation, such that the blood vessel can be rapidly opened for allowing the blood flow and shortening the anhepatic period. Then, further anastomosis can be completed by the traditional manual suture, and the vascular anastomosis device can be removed thereafter. The vascular anastomosis device of the present invention is simple in structure and is convenient to use. Through the present invention, the entire liver transplantation vascular anastomosis process is fast, safe, and reliable. The vascular anastomosis device of the present invention is particularly configured for rapid vascular anastomosis of liver transplantation in an effective manner by eliminating the excessively long anhepatic period and the related complications caused by manual suture operation during the liver transplantation.

DETAILED DESCRIPTION OF THE PREFERRED EMBODIMENT

The present invention will be described from the following accompanying drawings, and the specific embodiments.

A vascular anastomosis device for the magnetically assisted rapid liver transplantation is illustrated, wherein the vascular anastomosis device comprises a magnetic ring assembly and a base member assembly. The magnetic ring assembly comprises a O-shaped magnetic ring 1 and a C-shaped magnetic ring 2. The base member assembly comprises a O-shaped base member and a C-shaped base member.

Figure 1:
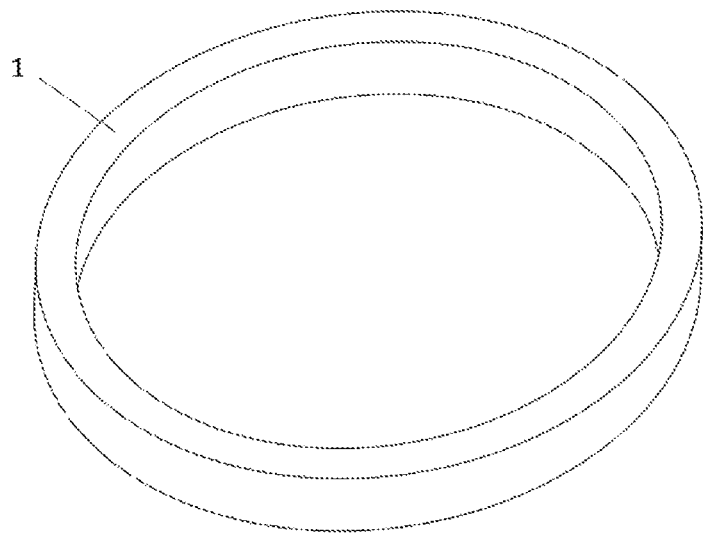
FIG. 1 is a perspective view of a O-shaped magnetic ring of a magnetic vascular anastomosis device for a rapid liver transplantation according to a preferred embodiment of the present invention.

As shown in FIG. 1, the O-shaped magnetic ring 1 can have a cylindrical shape or an oval shape.

Figure 2:
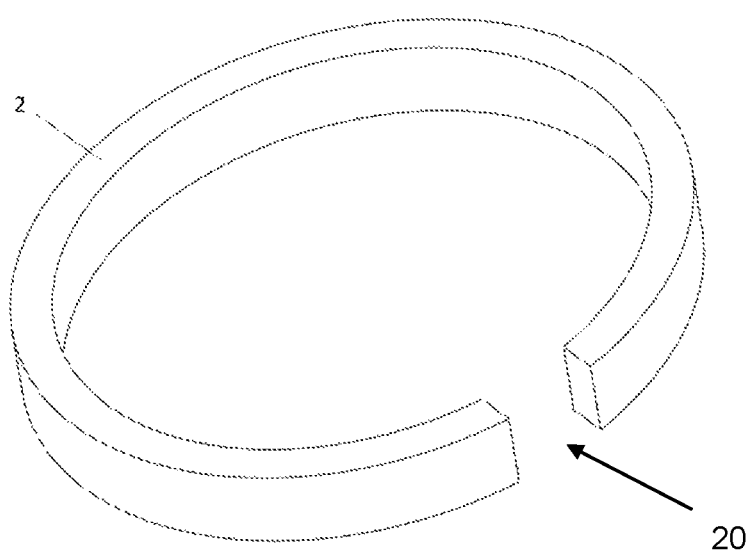
FIG. 2 is a perspective view of a C-shaped magnetic ring of the magnetic vascular anastomosis device for the rapid liver transplantation according to the above preferred embodiment of the present invention.

As shown in FIG. 2, the C-shaped magnetic ring 2 can have a cylindrical shape or an oval shape with a longitudinal through notch 20 extended from an inner circumferential wall of the C-shaped magnetic ring 2 to an outer circumferential wall thereof. Accordingly, a cross sectional size of the C-shaped magnetic ring 2 is the same as that of the O-shaped magnetic ring 1.

The O-shaped magnetic ring 1 and the C-shaped magnetic ring 2 can be made of magnetic material such as neodymium iron boron, aluminum nickel cobalt, ferrite, samarium cobalt, etc. The surface of the O-shaped magnetic ring 1 or the C-shaped magnetic ring 2 is treated and coated with titanium nitride, polytetrafluoroethylene, parylene, etc. An outer circumferential size of the O-shaped magnetic ring 1 or the C-shaped magnetic ring 2 matches an inner diameter of the blood vessel to be anastomosed.

Figure 3:
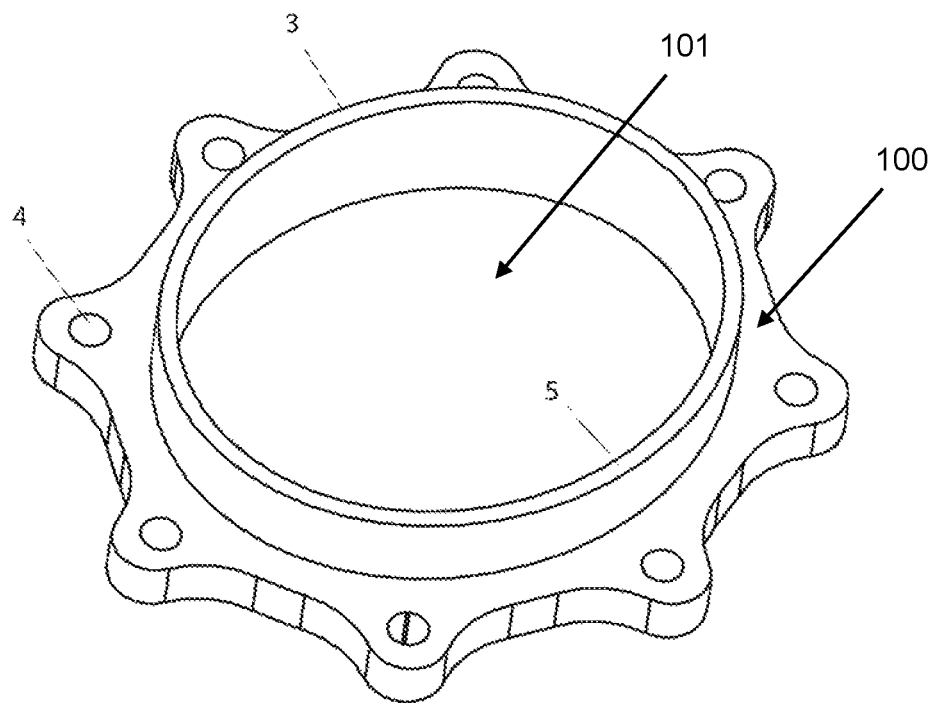
FIG. 3 is a perspective view of a slotted base member of the magnetic vascular anastomosis device for the rapid liver transplantation according to the above preferred embodiment of the present invention.
Figure 4:
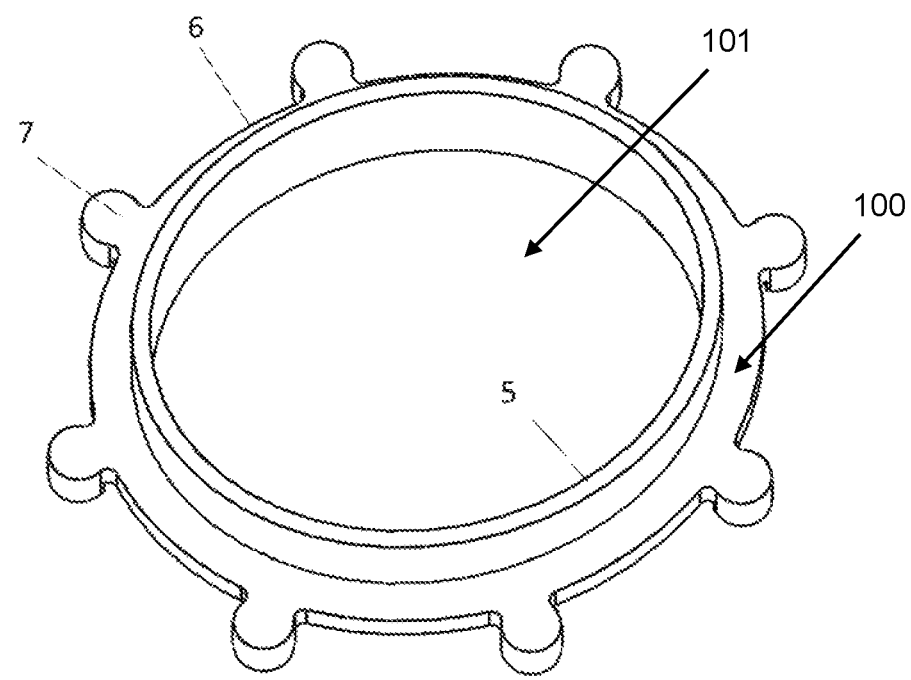
FIG. 4 is a perspective view of a columned base member of the magnetic vascular anastomosis device for the rapid liver transplantation according to the above preferred embodiment of the present invention.
Figure 5:
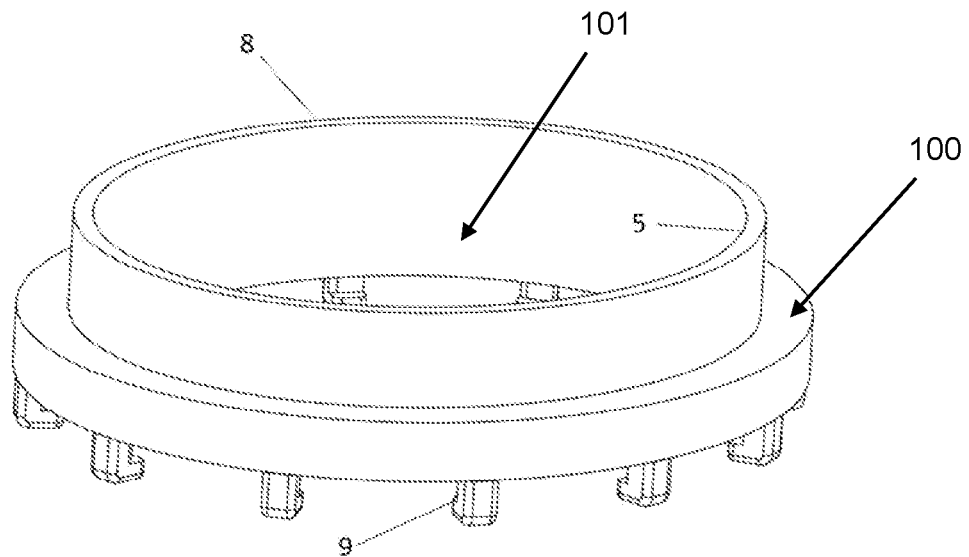
FIG. 5 is a perspective view of a hooked base member of the magnetic vascular anastomosis device for the rapid liver transplantation according to the above preferred embodiment of the present invention.

As shown in FIG. 3, FIG. 4, and FIG. 5, the O-shaped base member is detachably coupled at the O-shaped magnetic ring 1 for mounting at a liver blood vessel before it is broken. The O-shaped base member comprises a O-shaped base body 100 having a central through slot 101 and a O-shaped protrusion 5 integrally protruded from the O-shaped base body 100 at a position around the central through slot 101. Accordingly, the O-shaped protrusion 5 is upwardly and coaxially extended from an inner circumferential portion of the O-shaped base body 100 at an upper side thereof to encircle around the central through slot 101.

The cross sectional shape of the O-shaped protrusion 5 is the same as the cross sectional shape of the O-shaped magnetic ring 1. The size of the O-shaped protrusion 5 is equal or slightly smaller than the size of the O-shaped magnetic ring 1. The O-shaped base member further comprises a structure for proline threading provided at the O-shaped base body 100 outside the O-shaped protrusion 5. The structure for proline threading is extended out of the O-shaped base body 100 and is exposed when the O-shaped magnetic ring 1 is coupled at the O-shaped base body 100.

Figure 6:
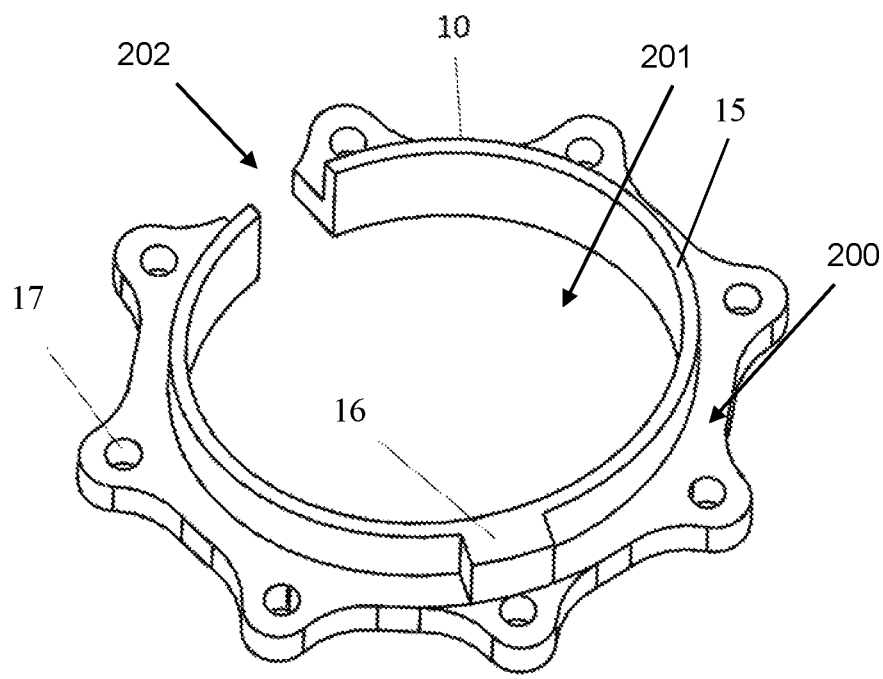
FIG. 6 is a perspective view of a C-shaped slotted base member of the magnetic vascular anastomosis device for the rapid liver transplantation according to the above preferred embodiment of the present invention.
Figure 7:
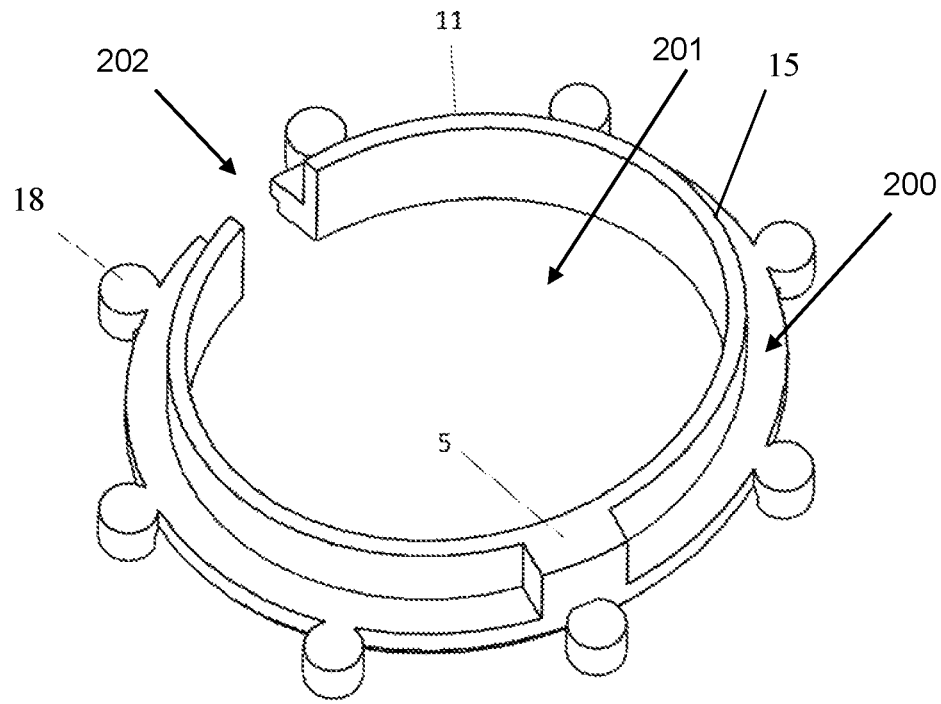
FIG. 7 is a perspective view of a C-shaped columned base member of the magnetic vascular anastomosis device for the rapid liver transplantation according to the above preferred embodiment of the present invention.
Figure 8:
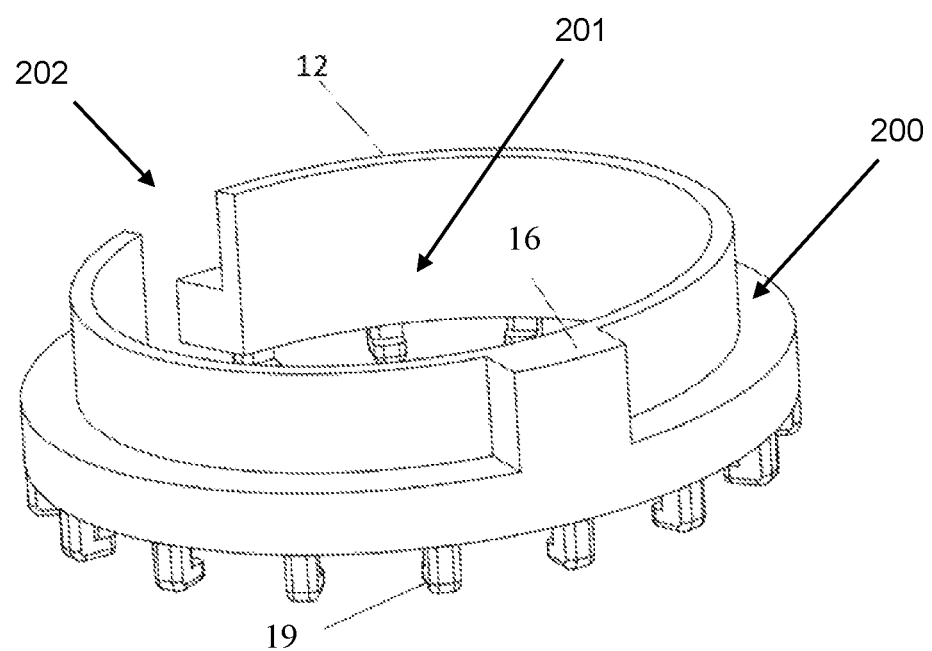
FIG. 8 is a perspective view of a C-shaped hooked base member of the magnetic vascular anastomosis device for the rapid liver transplantation according to the above preferred embodiment of the present invention.

As shown in FIG. 6, FIG. 7, and FIG. 8, the C-shaped base member and the C-shaped magnetic ring 2 are detachably coupled with each other for loading at the liver blood vessel before it is broken. The C-shaped base member comprises a C-shaped base body 200 having a central through slot 201 and comprises a C-shaped protrusion 15 integrally protruded from the C-shaped base body 200 at a position around the central through slot 201. Accordingly, the C-shaped protrusion 15 is upwardly and coaxially extended from an inner circumferential portion of the C-shaped base body 200 at an upper side thereof to encircle around the central through slot 201. The cross sectional shape of the C-shaped protrusion 15 is the same as the cross sectional shape of the C-shaped magnetic ring 2. The cross sectional size of the C-shaped protrusion 15 is equal or slightly smaller than the cross sectional size of the C-shaped magnetic ring 2. The C-shaped protrusion 15 has a gap extended from an inner circumferential wall of the C-shaped protrusion 15 to an outer circumferential wall thereof. The C-shaped base member further has a gap from an inner circumferential wall of the C-shaped base member to an outer circumferential wall thereof to communicate with the central through slot. The gap of the C-shaped protrusion 15 is aligned and communicated with the gap of the C-shaped base member. In other words, the C-shaped protrusion 15 and the C-shaped base body 200 form a through gap 202. The C-shaped base member further comprises a positioning member 16 integrally, outwardly and radially extended from the C-shaped protrusion 15, wherein a width of the positioning member 16 is equal or slightly smaller than a width of the longitudinal through notch 20 of the C-shaped magnetic ring 2. The C-shaped base member further comprises a structure for proline threading provided at the base member outside the C-shaped protrusion 15. The structure for proline threading is extended out of the C-shaped base body 200 and is exposed when the C-shaped magnetic ring 2 is coupled at the C-shaped base body 200.

Each of the O-shaped base member and the C-shaped base member can be made of metal material or polymer material, wherein the surface thereof can be treated or coated with titanium nitride, polytetrafluoroethylene, parylene, etc.

Figure 9:
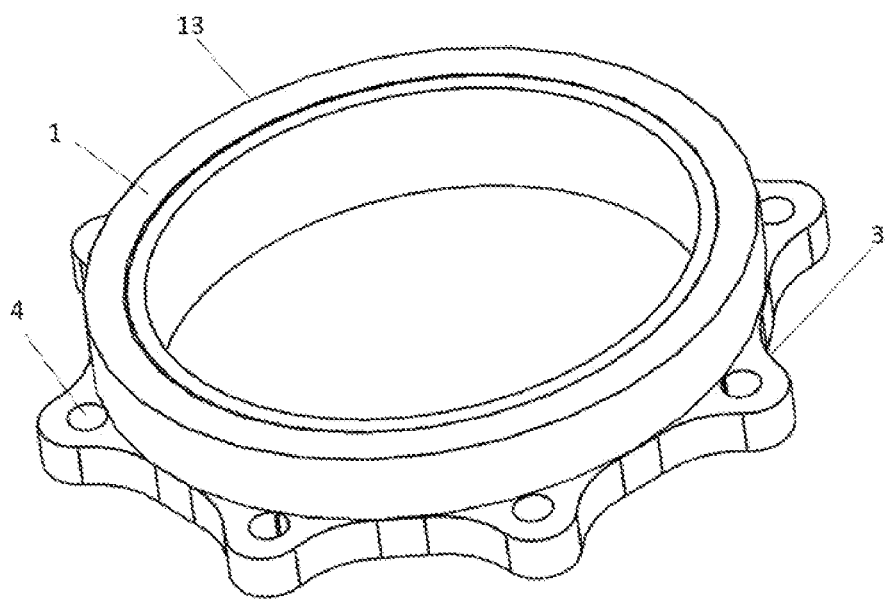
FIG. 9 is a perspective view of the magnetic vascular anastomosis device with the O-shaped magnetic ring for the rapid liver transplantation according to the above preferred embodiment of the present invention.
Figure 10:
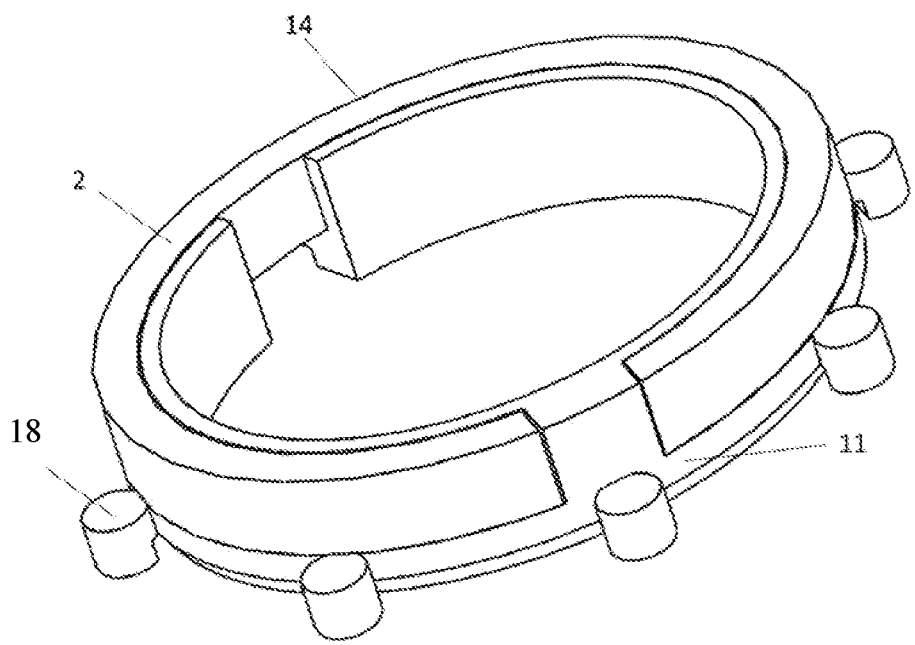
FIG. 10 is a perspective view of the magnetic vascular anastomosis device with the C-shaped magnetic ring for the rapid liver transplantation according to the above preferred embodiment of the present invention.

As shown in FIG. 9 and FIG. 10, the O-shaped magnetic ring 1 is sleeved or coaxially coupled with the O-shaped protrusion 5 to form a O-shaped magnetic assembling ring 13. In other words, the O-shaped magnetic ring 1 is coupled at the O-shaped base body 100 to encircle the O-shaped protrusion 5 within the O-shaped magnetic ring 1. Likewise, the C-shaped magnetic ring 2 is sleeved or coaxially coupled with the C-shaped protrusion 15 to form a C-shaped magnetic assembling ring 14, wherein the positioning member 16 is received at the longitudinal through notch 20 of the C-shaped magnetic ring 2. In other words, the C-shaped magnetic ring 2 is coupled at the C-shaped base body 200 to encircle the C-shaped protrusion 15 within the C-shaped magnetic ring 2. Accordingly, a magnetic pole of an exposed side of the O-shaped magnetic ring 1 is opposite to a magnetic pole of an exposed side of the C-shaped magnetic ring 2, such that the O-shaped magnetic ring 1 and the C-shaped magnetic ring 2 are magnetic attracted with each other.

According to the present invention, the structural configuration of the base member can be formed with a slotted type, a columned type and hooked type for being used in different surgical suture methods.

As shown in FIG. 3, the O-shaped base member is provided that the structure for proline threading comprises a plurality of first axial holes 4 outwardly and evenly distributed at an outer circumferential portion of the O-shaped base body 100 to form a O-shaped slotted base member 3. Each of the first axial holes 4 is used for fixing and knotting the suture when the blood vessel is flipped inside out.

As shown in FIG. 4, the O-shaped base member is provided that the structure for proline threading comprises a plurality of first axial columns 7 outwardly and evenly distributed at an outer circumferential portion of the O-shaped base body 100 to form a O-shaped columned base member 6. Each of the first axial columns 7 is used for retaining the suture when the blood vessel is flipped inside out, so as to retain the blood vessel at the flipped condition. Comparing to the slot structure in FIG. 3, the column structure in FIG. 4 can prevent the operation of knotting the sutures one by one.

As shown in FIG. 5, the O-shaped base member is provided that the structure for proline threading comprises a plurality of first hooks 9 downwardly, axially and evenly distributed at a bottom side of the O-shaped base body 100, i.e. opposite to the O-shaped protrusion 5, to form a O-shaped hooked base member 8, wherein hooking ends of the first hooks 9 are extended toward a center of the central through slot 101 of the O-shaped base body 100 of the O-shaped base member. Each of the first hooks 9 is used for retaining the suture when the blood vessel is flipped inside out. Comparing to the column structure in FIG. 4, the hook structure in FIG. 5 can provide better suture retention to prevent the suture being slipped out of the base member. Comparing to the slot structure in FIG. 3, the hook structure in FIG. 5 can prevent the operation of knotting the sutures one by one.

As shown in FIG. 6, the C-shaped base member is provided that the structure for proline threading comprises a plurality of second axial holes 17 outwardly and evenly distributed at an outer circumferential portion of the C-shaped base body 200 to form a C-shaped slotted base member 10. Each of the second axial holes 17 is used for fixing and knotting the suture when the blood vessel is flipped inside out.

As shown in FIG. 7, the C-shaped base member is provided that the structure for proline threading comprises a plurality of second axial columns 18 outwardly and evenly distributed at an outer circumferential portion of the C-shaped base body 200 to form a C-shaped columned base member 11. Each of the second axial columns 18 is used for retaining the suture when the blood vessel is flipped inside out, so as to retain the blood vessel at the flipped condition. Comparing to the slot structure in FIG. 6, the column structure in FIG. 7 can prevent the operation of knotting the sutures one by one.

As shown in FIG. 8, the C-shaped base member is provided that the structure for proline threading comprises a plurality of second hooks 19 downwardly, axially and evenly distributed at a bottom side of the C-shaped base body 200, i.e. opposite to the C-shaped protrusion 15, to form a C-shaped hooked base member 12, wherein hooking ends of the second hooks 19 are extended toward a center of the central through slot 201 of the C-shaped base body 200 of the C-shaped base member. Each of the second hooks 19 is used for retaining the suture when the blood vessel is flipped inside out. Comparing to the column structure in FIG. 7, the hook structure in FIG. 8 can provide better suture retention to prevent the suture being slipped out of the base member. Comparing to the slot structure in FIG. 6, the hook structure in FIG. 8 can prevent the operation of knotting the sutures one by one.

According to the above structures, the operation of the present invention for connecting first and second blood vessels together is shown as follows:

During the surgery operation, the O-shaped magnetic ring 1 and the O-shaped base member are coupled at the first blood vessel, especially for the donor liver blood vessel, wherein the O-shaped magnetic ring 1 is retained at a vessel wall of the first blood vessel by one of the following configurations:

The O-shaped magnetic ring 1 and the O-shaped slotted type base member 3 are coupled to form the O-shaped slotted magnetic assembling ring, wherein after the O-shaped slotted magnetic assembling ring is arranged for mounting at the first blood vessel, the vessel wall thereof is flipped inside out to cover the O-shaped protrusion 5, such that the proline threading is continuously applied through the first axial holes 4 to suture the vessel wall, so as to retain the O-shaped magnetic ring 1 at the vessel wall.

The O-shaped magnetic ring 1 and the O-shaped column type base member 6 are coupled to form the O-shaped columned magnetic assembling ring, wherein after the O-shaped columned magnetic assembling ring is arranged for mounting at the first blood vessel, the vessel wall thereof is flipped inside out to cover the O-shaped protrusion 5, such that the proline threading is continuously applied round the first axial columns 7 to suture the vessel wall, so as to retain the O-shaped magnetic ring 1 at the vessel wall.

The O-shaped magnetic ring 1 and the O-shaped hook type base member 8 are coupled to form the O-shaped hooked magnetic assembling ring, wherein after the O-shaped hooked magnetic assembling ring is arranged for mounting at the first blood vessel, the vessel wall thereof is flipped inside out to cover the O-shaped protrusion 5, such that the proline threading is continuously applied round the first hooks 9 to suture the vessel wall, so as to retain the O-shaped magnetic ring 1 at the vessel wall.

The C-shaped magnetic ring 2 and the C-shaped base member are coupled with each other for mounting at the second blood vessel, especially for the receptor liver lateral blood vessel, is broken (before the recipient liver blood vessel is broken, the longitudinal through notch 20 of the C-shaped magnetic ring 2 can be mounted at the second blood vessel), wherein the C-shaped magnetic ring 2 is retained at a vessel wall of the second blood vessel by one of the following configurations:

The C-shaped magnetic ring 2 and the C-shaped slotted type base member 10 are coupled to form the C-shaped slotted magnetic assembling ring, wherein after the C-shaped slotted magnetic assembling ring is arranged for mounting at the second blood vessel, the vessel wall thereof is flipped inside out to cover the C-shaped protrusion 15, such that the proline threading is continuously applied through the second axial holes 17 to suture the vessel wall, so as to retain the C-shaped magnetic ring 2 at the vessel wall.

The C-shaped magnetic ring 2 and the C-shaped column type base member 11 are coupled to form the O-shaped columned magnetic assembling ring, wherein after the C-shaped columned magnetic assembling ring is arranged for mounting at the second blood vessel, the vessel wall thereof is flipped inside out to cover the C-shaped protrusion 15, such that the proline threading is continuously applied round the second axial columns 18 to suture the vessel wall, so as to retain the C-shaped magnetic ring 2 at the vessel wall.

The C-shaped magnetic ring 2 and the C-shaped hook type base member 12 are coupled to form the C-shaped hooked magnetic assembling ring, wherein after the C-shaped hooked magnetic assembling ring is arranged for mounting at the second blood vessel, the vessel wall thereof is flipped inside out to cover the O-shaped protrusion 5, such that the proline threading is continuously applied round the second hooks 19 to suture the vessel wall, so as to retain the C-shaped magnetic ring 2 at the vessel wall.

After the C-shaped magnetic ring 2 is retained at the vessel wall, the receptor liver lateral blood vessel is blocked, such that the donor liver blood vessel can be cut off to remove the receptor liver. Then, prepare anastomosis of the receptor liver lateral blood vessel with the donor liver blood vessel. The O-shaped magnetic ring 1 at the donor vessel wall is magnetically coupled at the C-shaped magnetic ring 2 at the receptor vessel wall to complete the preliminary anastomosis of the first and second blood vessels. Then, open up the blood vessels to allow blood flow to the liver, such that the anhepatic phase of the recipient is finished. Then, after completing the anastomosis by the traditional manual suture method, the O-shaped magnetic ring 1, C-shaped magnetic ring 2 and their related base members of the vascular anastomosis device are then withdrawn, and the entire liver transplantation vascular anastomosis process is completely finished.

In summary, the vascular anastomosis device of the present invention is arranged for magnetically-assisting the liver transplantation in a rapid manner, wherein by using the magnetical attraction between magnetic rings to achieve rapid preliminary anastomosis in liver transplantation, such that the blood vessel can be rapidly opened for allowing the blood flow and shortening the anhepatic period. Then, further anastomosis can be completed by the traditional manual suture, and the vascular anastomosis device can be removed thereafter. The vascular anastomosis device of the present invention is simple in structure and is convenient to use. Through the present invention, the entire liver transplantation vascular anastomosis process is fast, safe, and reliable. The vascular anastomosis device of the present invention is particularly configured for rapid vascular anastomosis of liver transplantation in an effective manner by eliminating the excessively long anhepatic period and the related complications caused by manual suture operation during the liver transplantation. The vascular anastomosis device of the present invention can also apply for different operations involving vascular anastomosis such as kidney transplantation, lung transplantation, heart transplantation, and maxillofacial surgery.

What is claimed is:
1. A magnetic vascular anastomosis device for rapid liver transplantation, comprising:
   a O-shaped magnetic ring (1), which has a cylindrical shape or an oval shape;
   a C-shaped magnetic ring (2) having a longitudinal through notch (20) extended from an inner circumferential wall of the C-shaped magnetic ring (2) to an outer circumferential wall thereof, wherein a cross sectional shape of the O-shaped magnetic ring (1) is the same as a cross sectional shape of the C-shaped magnetic ring (2);

a O-shaped base member comprising a O-shaped base body (100) having a central through slot (101), a O-shaped protrusion (5) extended from the base body at a position around the central through slot (101), and a structure for proline threading provided at the O-shaped base body (100) outside the O-shaped protrusion (5); and a C-shaped base member comprising a C-shaped base body (200) having a central through slot (201), a C-shaped protrusion (15) extended from the base body at a position around the central through slot (201), and a structure for proline threading provided at the C-shaped base body (200) outside the C-shaped protrusion (15), wherein the C-shaped protrusion (15) and the C-shaped base body (200) form a through gap (202), wherein the C-shaped base member further comprises a positioning member (16) integrally, outwardly and radially extended from the C-shaped protrusion (15), wherein a width of the positioning member (16) is equal or slightly smaller than a width of the longitudinal through notch (20) of the C-shaped magnetic ring (2).

2. The magnetic vascular anastomosis device, as recited in claim 1, wherein each of the O-shaped magnetic ring (1) and the C-shaped magnetic ring (2) is made of neodymium iron boron, aluminum nickel cobalt, ferrite or samarium cobalt, wherein a surface of each of the O-shaped magnetic ring (1) and the C-shaped magnetic ring (2) is coated with titanium nitride, polytetrafluoroethylene or parylene, wherein an outer diameter of each of the O-shaped magnetic ring (1) and the C-shaped magnetic ring (2) matches with an inner diameter of a blood vessel to be anastomosed.

3. The magnetic vascular anastomosis device, as recited in claim 1, wherein each of the C-shaped base member and the C-shaped base member is made of metal material or a polymer material, and a surface of each of the C-shaped base member and the C-shaped base member is coated with titanium nitride, polytetrafluoroethylene, or parylene.

4. The magnetic vascular anastomosis device, as recited in claim 1, wherein, for the O-shaped base member, the structure for proline threading comprises a plurality of first axial holes (4) outwardly and evenly distributed at an outer circumferential portion of the O-shaped base body (100) to form a O-shaped slotted base member (3).

5. The magnetic vascular anastomosis device, as recited in claim 1, wherein, for the O-shaped base member, the structure for proline threading comprises a plurality of radial columns (7) outwardly and evenly distributed at an outer circumferential portion of the base member to form a O-shaped columned base member (6).

6. The magnetic vascular anastomosis device, as recited in claim 1, wherein, for the O-shaped base member, the structure for proline threading comprises a plurality of first hooks (9) downwardly and evenly distributed at a bottom side of the O-shaped base body (100) to form a O-shaped hooked base member (8).

7. The magnetic vascular anastomosis device, as recited in claim 1, wherein, for the C-shaped base member, the structure for proline threading comprises a plurality of radial holes (17) outwardly and evenly distributed at an outer circumferential portion of the C-shaped base body (200) to form a C-shaped slotted base member (10).

8. The magnetic vascular anastomosis device, as recited in claim 1, wherein, for the C-shaped base member, the structure for proline threading comprises a plurality of radial columns (18) outwardly and evenly distributed at an outer circumferential portion of the C-shaped base body (200) to form a C-shaped columned base member (11).

9. The magnetic vascular anastomosis device, as recited in claim 1, wherein, for the C-shaped base member, the structure for proline threading comprises a plurality of second hooks (19) downwardly and evenly distributed at a bottom side of the C-shaped base body (200) to form a C-shaped hooked base member (12), wherein hooking ends of the second hooks (19) are extended toward a center of the central through slot (201) of the C-shaped base body (200).

10. The magnetic vascular anastomosis device, as recited in claim 1, wherein the O-shaped magnetic ring (1) is coaxially coupled with the O-shaped protrusion (5) to form a O-shaped magnetic assembling ring (13), wherein the C-shaped magnetic ring (2) is coaxially coupled with the C-shaped protrusion (15) to form a C-shaped magnetic assembling ring (14).

11. The magnetic vascular anastomosis device, as recited in claim 1, wherein a magnetic pole of an exposed side of the O-shaped magnetic ring (1) is opposite to a magnetic pole of an exposed side of the C-shaped magnetic ring (2), such that the O-shaped magnetic ring (1) and the C-shaped magnetic ring (2) are magnetically attracted with each other.

12. The magnetic vascular anastomosis device, as recited in claim 1, wherein the O-shaped magnetic ring (1) and the C-shaped magnetic ring (2) are made of magnetic material.

13. The magnetic vascular anastomosis device, as recited in claim 1, wherein a cross sectional shape of the O-shaped protrusion (5) is the same as the cross sectional shape of the O-shaped magnetic ring (1), wherein a cross sectional size of the O-shaped protrusion (5) is equal or slightly smaller than a cross sectional size of the O-shaped magnetic ring (1).

14. The magnetic vascular anastomosis device, as recited in claim 1, wherein a cross sectional shape of the C-shaped protrusion (15) is the same as the cross sectional shape of the C-shaped magnetic ring (2), wherein a cross sectional size of the C-shaped protrusion (15) is equal or slightly smaller than a cross sectional size of the C-shaped magnetic ring (2).

15. The magnetic vascular anastomosis device, as recited in claim 1, wherein the O-shaped protrusion (5) is upwardly and coaxially extended from an inner circumferential portion of the O-shaped base body (100) at an upper side thereof to encircle around the central through slot (101) of the O-shaped base body (100).

16. The magnetic vascular anastomosis device, as recited in claim 1, wherein the C-shaped protrusion (15) is upwardly and coaxially extended from an inner circumferential portion of the C-shaped base body (200) at an upper side thereof to encircle around the central through slot (201) of the C-shaped base body (200).

17. The magnetic vascular anastomosis device, as recited in claim 1, wherein the O-shaped magnetic ring (1) is coupled at the O-shaped base body (100) to encircle the O-shaped protrusion (5) within the O-shaped magnetic ring (1).

18. The magnetic vascular anastomosis device, as recited in claim 1, wherein the C-shaped magnetic ring (2) is coupled at the C-shaped base body (200) to encircle the C-shaped protrusion (15) within the C-shaped magnetic ring (2).

19. The magnetic vascular anastomosis device, as recited in claim 1, wherein, for the O-shaped base member, the structure for proline threading is extended out of the O-shaped base body (100) and is exposed when the O-shaped magnetic ring (1) is coupled at the O-shaped base body (100).

20. The magnetic vascular anastomosis device, as recited in claim 1, wherein, for the C-shaped base member, the structure for proline threading is extended out of the C-shaped base body (200) and is exposed when the C-shaped magnetic ring (2) is coupled at the C-shaped base body (200).

\* \* \* \* \*